(12) United States Patent
Duane

(10) Patent No.: US 6,890,340 B2
(45) Date of Patent: May 10, 2005

(54) APPARATUS FOR TEMPORARY INTRALUMINAL PROTECTION

(75) Inventor: Patrick J. Duane, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 376 days.

(21) Appl. No.: 09/998,766

(22) Filed: Nov. 29, 2001

(65) Prior Publication Data

US 2003/0100918 A1 May 29, 2003

(51) Int. Cl.⁷ .............................................. A61M 29/00
(52) U.S. Cl. ...................................................... 606/200
(58) Field of Search ................................ 606/200, 194, 606/127; 623/1.11

(56) References Cited

U.S. PATENT DOCUMENTS

| 4,425,908 A | 1/1984 | Simon |
| 4,794,928 A | 1/1989 | Kletschka |
| 5,108,419 A | 4/1992 | Reger et al. |
| 5,649,953 A | 7/1997 | Lefebvre |
| 5,733,294 A | 3/1998 | Forber et al. |
| 5,814,064 A | 9/1998 | Daniel et al. |
| 6,361,545 B1 * | 3/2002 | Macoviak et al. ........... 606/200 |
| 6,605,102 B1 * | 8/2003 | Mazzocchi et al. ......... 606/200 |
| 2001/0044634 A1 | 11/2001 | Don Michael et al. |
| 2002/0138094 A1 * | 9/2002 | Borillo et al. .............. 606/200 |

FOREIGN PATENT DOCUMENTS

| EP | 1 123 688 A2 | 8/2001 |
| WO | WO 96/01591 A1 | 1/1996 |
| WO | WO 00/16705 A1 | 3/2000 |
| WO | WO 01/15629 A1 | 3/2001 |
| WO | WO 01/67989 A2 | 9/2001 |
| WO | WO 02/43595 A2 | 6/2002 |

* cited by examiner

Primary Examiner—(Jackie) Tan-Uyen T. Ho

(57) ABSTRACT

A temporary intraluminal protection apparatus for use during interventional catheterization procedures, such as angioplasty or stent deployment. A protection element is mounted near the distal end of an elongate shaft, and includes a concave proximal end. To protect distal side branches adjacent a treatment site, the distal end of an inflated balloon of a balloon catheter is receivable within the concave proximal end of the protection element. A tubular actuator slides over the shaft to engage the protection element, causing transformation thereof between an open configuration and a closed configuration.

4 Claims, 3 Drawing Sheets

APPARATUS FOR TEMPORARY INTRALUMINAL PROTECTION

FIELD OF THE INVENTION

The present invention relates generally to intraluminal devices for protecting vessels in a patient from downstream passage of embolic debris that maybe generated during an interventional procedure. The invention concerns either a filter or an occluder mounted on a tubular shaft or a guidewire.

BACKGROUND OF THE INVENTION

A variety of treatments exists for dilating or removing atherosclerotic plaque in blood vessels. The use of an angioplasty balloon catheter is common in the art as a minimally invasive treatment to enlarge a stenotic or diseased blood vessel. When applied to the vessels of the heart, this treatment is known as percutaneous transluminal coronary angioplasty, or PTCA. To provide radial support to the treated vessel in order to prolong the positive effects of PTCA, a stent may be implanted in conjunction with the procedure.

Thrombectomy is a minimally invasive technique for removal of an entire thrombosis or a sufficient portion of the thrombosis to enlarge the stenotic or diseased blood vessel and may be accomplished instead of a PTCA procedure. Atherectomy is another well known minimally invasive procedure that mechanically cuts or abrades a stenosis within the diseased portion of the vessel. Alternatively, ablation therapies use laser or RF signals to superheat or vaporize the thrombus within the vessel. Emboli loosened during such procedures may be removed from the patient through the catheter.

During each of these procedures, there is a risk that emboli dislodged by the procedure will migrate through the circulatory system and cause infarction or stroke. Thus, clinicians have approached prevention of escaped emboli through use of occlusion devices, filters, lysing and aspiration techniques. For example, it is known to remove the embolic material by suction through an aspiration lumen in the treatment catheter or by capturing emboli in a filter or occlusion device positioned distal of the treatment area.

SUMMARY OF THE INVENTION

The present invention is a temporary protection apparatus for use in intraluminal procedures. The device includes a protection element mounted adjacent the distal end of an elongate flexible shaft, such as a guidewire or a hollow tube. The protection element may be pre-mounted about the shaft prior to insertion of the apparatus into the patient. Alternatively, a shaft in accordance with the invention may be inserted without the protection element, which can be slid over the shaft later. The self-expanding protection element may be a filter that captures emboli while allowing body fluid to pass therethrough, or it may be an occluder that temporarily interrupts all fluid flow through a body vessel. A proximal concavity in the protection element permits it to be located about the distal end of an angioplasty or stent delivery balloon such that distally adjacent side branches can be protected. A tubular actuator maybe slid over the shaft to abut the protection element within the proximal concavity. Further distal advancement of the actuator causes the protection element to reversibly transform from an open configuration to a closed configuration.

BRIEF DESCRIPTION OF THE DRAWINGS

These and other features, aspects and advantages of the present invention will become better understood with reference to the following description, appended claims, and accompanying drawings where:

DETAILED DESCRIPTION OF THE INVENTION

Figure 1:
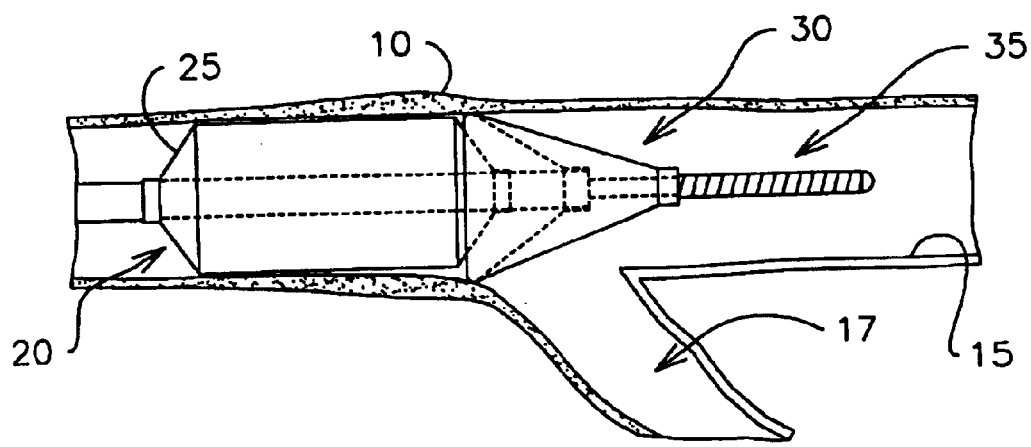
FIG. 1 is an illustration of a temporary protection apparatus in accordance with the invention deployed adjacent an interventional catheter within a longitudinally sectioned portion of a body vessel.

FIG. 1 illustrates an example of the invention during use. Body vessel 10 includes lumen 15 and side branch 17. Catheter 20 is shown with balloon 25 inflated to dilate a narrowing in vessel 10 immediately proximal to side branch 17. Protection apparatus 30 is deployed, or opened, against lumen 15. In this example, shaft 35 comprises a guidewire extending through both catheter 20 and protection apparatus 30.

Figures 2, 3:
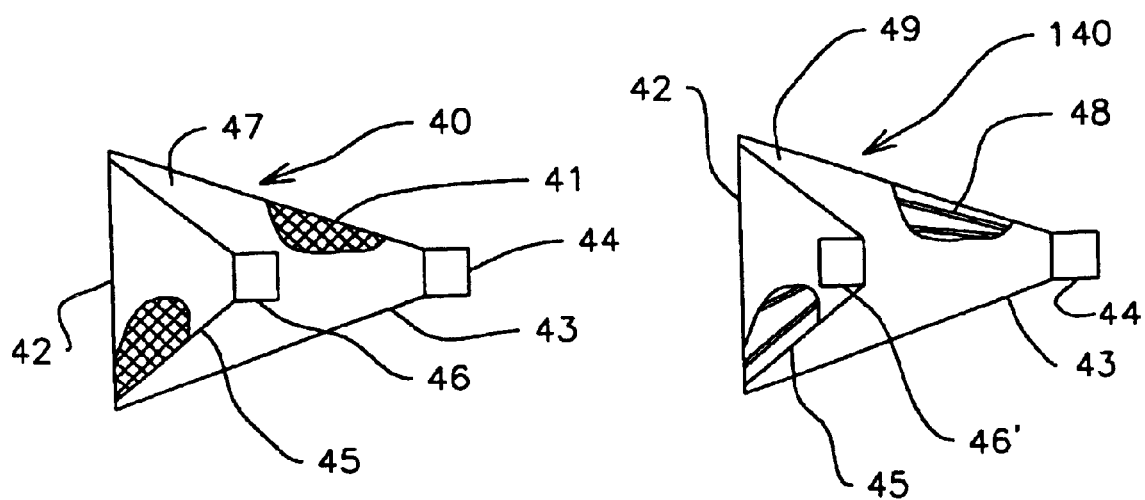
FIG. 2 is an illustration of a longitudinal section of a protection element in accordance with the invention.
FIG. 3 is an illustration of a longitudinal section of an alternative protection element in accordance with the invention.

FIG. 2 shows protection element 40, which comprises a tubular braid 41 that has been formed into a shape resembling two nested cones having different heights and being joined at their bases to form ring portion 42 at the proximal end. Outer body 43 is generally conical in shape and tapers in a distal direction from ring portion 42 to distal open apex 44, which is adapted to be fixedly or slidingly coupled to shaft 35. Inner body 45 is shorter than outer body 43 and extends there within. Inner body 45 is also generally conical in shape and tapers in a distal direction from ring portion 42 to proximal open apex 46, which is adapted to be slidingly coupled to shaft 35. Braid 41 comprises filaments of biocompatible thermoplastics or metals such as stainless steel or nitinol (NiTi), which can be heat treated to create mechanical memory in the shape of protection element 40. During heating at a temperature suitable for the selected material, braid 41 can be formed into the shape of protection element 40 by being held over a shaped core, or mandrel, or it may be contained in a shaped mold cavity.

Protection element 40 may be a filter device that relies on pores formed in braid 41. The device may capture emboli within the concave proximal end formed by inner body 45, or within the volume formed between inner body 45 and outer body 43, or at both locations. Selected pores of inner body 45 may be enlarged (not shown) by the use of additional pins or other forming elements during the heat treating process. Enlarged inlet pores can allow embolic debris to pass through inner body 45 and be collected in the volume formed between inner body 45 and outer body 43. Proximal apex 46 and distal apex 44 may include metal or plastic tubular bands joined to the respective body portions. For example, open apexes 44,46 may incorporate radiopaque metal bands soldered, brazed or glued to the respective ends of braid 41, which can lie within, without or in abutment with the metal bands. Alternatively, solder, braze or adhesive may be used without bands to join the ends of braid 41 and thereby form open apexes 44,46.

Alternatively, as shown in FIG. 2, braid 41 may be a support structure for porous filter material 47. Filter material 47 may have one or more layers secured to inner body 45 and/or outer body 43, and the layer(s) may be located on inner surfaces, outer surfaces, both surfaces, or parts of surfaces. In one exemplary embodiment, protection element 40 may include braid 41, which has large pores, and filter material 47 which covers only the inner surface of outer body 43. In this example, emboli can pass easily through the large pores of inner body 45 and be caught inside outer body 43 by filter material 47.

Protection element 140, shown in FIG. 3, is an alternative embodiment of the invention, and is similar to protection element 40 with the following differences. In protection element 140, proximal apex 46' is inverted (as compared to proximal apex 46) such that it lies within inner body 45. Protection element 140 is a temporary occluder, wherein struts 48 provide support for non-porous material 49, which interrupts the flow of bodily fluids through vessel 10. Struts 48 may be any wire-like components that support non-porous material 49 in the memorized shape of protection elements 40, 140, as described above. Struts 48 generally lie in planes radially arranged about a central axis of the apparatus, and may include wire-forms or portions of a slotted tube. Non-porous material 49 may be a flexible elastic or inelastic film attached to struts 48. Alternatively, non-porous material 49 may comprise a continuous film coating applied to struts 48 as an elastomer dissolved in a dipping solution. Any combination of the features shown in protection elements 40, 140 is possible. For example, an occlusive protection element may have a braided support structure with an inverted proximal apex and a non-porous coating applied only to the outer body.

Figure 4:
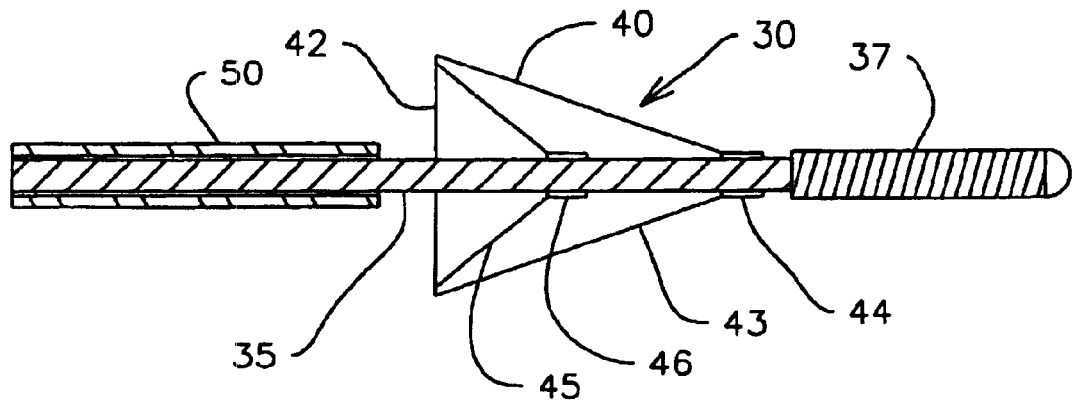
FIG. 4 is an illustration of a longitudinal section of a temporary protection apparatus and an actuator in accordance with the invention, shown with the protection element in an open configuration.

FIG. 4 shows protection apparatus 30 and actuator 50. Protection element 40 is mounted about shaft 35, which is shown as a standard-type steerable guidewire which includes an elongate shaft having a distal region surrounded by a flexible tubular element, such as a coiled spring. Alternatively, shaft 35 can be a hollow tube, such as a catheter made of suitable medical grade plastics, metals or a combination of such materials. In the embodiment shown, distal open apex 44 and proximal open apex 46 are both slidably coupled to shaft 35. Shaft 35 may first be introduced into the patient's vessel without protection element 40. Then, at the discretion of the clinician, protection element 40 may be slid onto the proximal end (not shown) of shaft 35. Actuator 50 can be fabricated as any type of pushable sheath in accordance with the field of catheters, including the use of suitable plastic and metal materials. Actuator 50 is a tubular push member slidingly disposed about shaft 35 proximal to protection element 40 and useable to advance protection element 40 to the distal end of shaft 35. There, the coiled spring acts as stop 37, which prevents protection element 40 from sliding distally along shaft 35. Alternatively, stop 37 may be a band or other protrusion on shaft 35. Optionally, distal open apex 44 maybe fixedly coupled to shaft 35 using solder, braze alloys or adhesives, such as cyanoacrylates. Distal open apex 44 may also be rotatably mounted on shaft 35 between two stops, which would prevent axial movement of distal open apex 44. Proximal open apex 46 is slidably coupled to shaft 35, regardless of whether distal open apex 44 is fixed or slidable. As shown in FIGS. 1–4, protection element 40 is self-expanded into an open configuration such that ring portion 42 is capable of sealing engagement with lumen 15.

Figure 5:
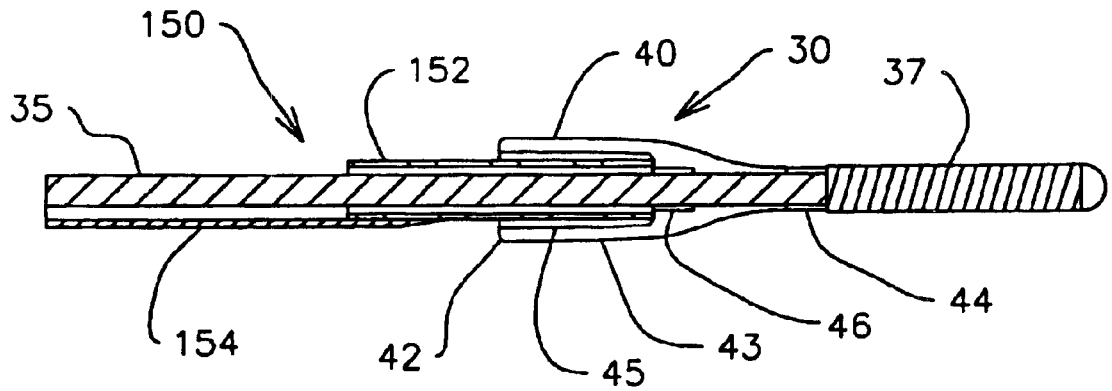
FIG. 5 is an illustration of a longitudinal section of a temporary protection apparatus and an alternative actuator embodiment in accordance with the invention, shown with the protection element in a closed configuration.

FIG. 5 shows protection apparatus 30 and alternative actuator 150, which has elongate, wire-like proximal shaft 154 and relatively short tubular distal section 152. Actuator 150 is shown having pushed proximal open apex 46 towards distal open apex 44 until protection element 40 is in a closed configuration that compactly envelopes shaft 35 and a distal portion of actuator 150. In the closed configuration of protection element 40, ring portion 42 is closed about actuator 50, forming a proximal folded lip of material connecting outer body 43 with inner body 45. The transformation of protection element 40 from an open configuration to a closed configuration is accomplished by the clinician pulling shaft 35 while pushing actuator 150. This transformation can be reversed by removing the distal pressure applied by actuator 150 to proximal open apex 46, which will permit protection element 40 to expand itself back into the open configuration. In the example shown, while actuator 150 pushes proximal open apex 46 distally, stop 37 restrains slidable distal open apex 44 against distal movement. Alternatively, inverted proximal open apex 46' may be incorporated into the shape of protection element 40, thus providing an exposed proximal end for selective abutment with actuator 150.

Because inner body 45 is shorter than outer body 43, displacement of proximal open apex 46 towards distal open apex 44 applies a longitudinal tension load to inner body 45 and a longitudinal compression load to outer body 43. These combined loads work to reduce the diameter of ring portion 42. Under these conditions, the memorized shape imparted to protection element 40 helps keep outer body 43 from buckling or bulging radially outward. During transformation of protection element 40 between open and closed configurations, ring portion 42 may act as a rolling diaphragm, such that some material may move from one body, through ring portion 42, to the other body. The closed configuration of protection apparatus 30 has a reduced profile, which is useful for preventing luminal injury whenever the device is moved through the patient's vessels.

Figure 6:
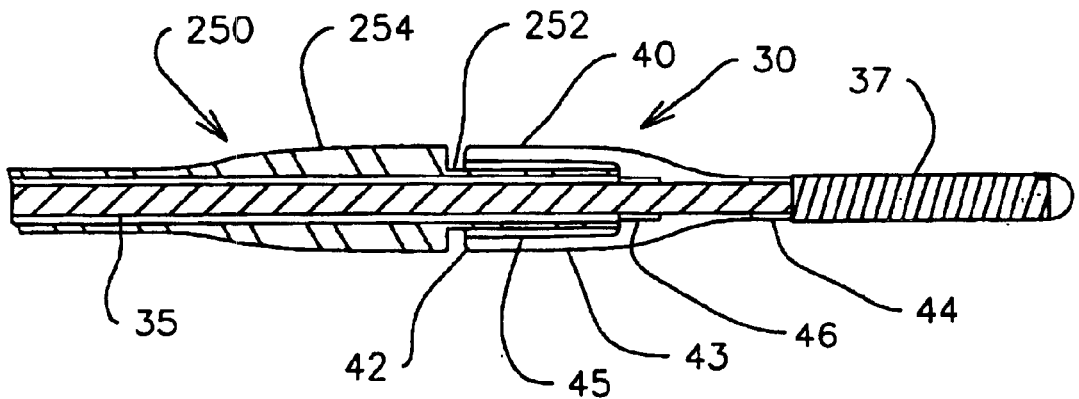
FIG. 6 is an illustration of a longitudinal section of a temporary protection apparatus and a third actuator embodiment in accordance with the invention, shown with the protection element in a closed configuration.

FIG. 6 shows protection apparatus 30 and alternative actuator 250 which has actuator distal portion 252 and actuator proximal portion 254. Actuator distal portion 252 has a length and a diameter sized to fit within inner body 45, when protection element 40 is in the closed configuration. At least a region of actuator proximal portion 254 that abuts actuator distal portion 252 has a diameter that nearly matches the contracted diameter of ring portion 42 when protection element 40 is in the closed configuration. The step-up in diameter between actuator distal portion 252 and actuator proximal portion 254 provides a smooth transition between actuator 250 and protection element 40. Such a transition is useful when protection apparatus 30 is drawn proximally through the vessel 10 because it can prevent ring portion 42 from catching on anatomic protrusions or implanted devices, such as stents.

Figure 7:
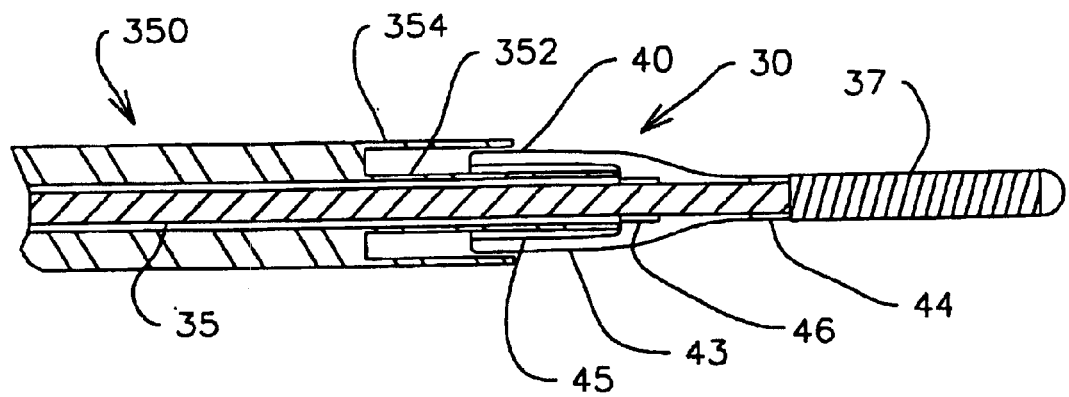
FIG. 7 is an illustration of a longitudinal section of a temporary protection apparatus and fourth actuator embodiment in accordance with the invention, shown with the protection element in a closed configuration.
Figure 8:
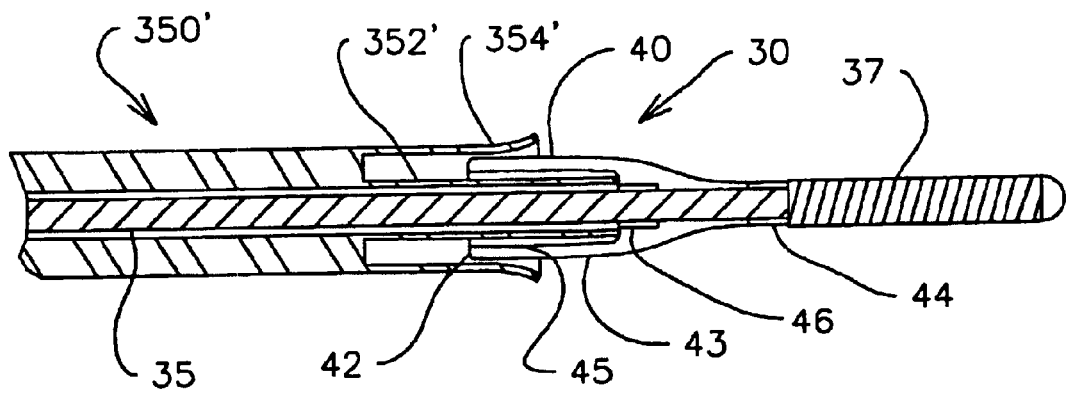
FIG. 8 is an illustration of a longitudinal section of a temporary protection apparatus and fifth actuator embodiment in accordance with the invention, shown with the protection element in a closed configuration.

FIG. 7 shows protection apparatus 30 and alternative actuator 350 which has actuator distal portion 352 and actuator sheath portion 354. Actuator distal portion 352 has a diameter sized to fit within inner body 45 when protection element 40 is in the closed configuration. Actuator sheath portion 354 extends over a proximal region of actuator distal portion 352 to create an annular pocket capable of receiving at least a proximal portion of protection element 40, when it is in the closed configuration. Alternatively, actuator sheath portion 354 can be a separate sheath element (not shown) slidably disposed about an actuator such as actuator 50. Actuator sheath portion 354 can help retain protection element 40 in the closed configuration. Once protection element 40 is engaged within actuator sheath portion 354, further advancement of actuator 350 over shaft 35 can cause protection element 40 to become more deeply engaged within the annular pocket. The action that causes deeper engagement of protection element 40 within actuator sheath portion 354 can comprise a rolling diaphragm effect wherein the closed configuration remains at the same diameter while material rolls from outer body 43, through ring portion 42, to inner body 45. FIG. 8 shows protection apparatus 30 wherein alternative actuator 350' has actuator distal portion 352' and flared actuator sheath portion 354'. Actuator 350' is similar to actuator 350 except that sheath portion 354' is flared at its distal end to facilitate engagement with ring portion 42 when protection element 40 is in the closed configuration.

The invention may be used according to the following example. Protection apparatus 30 is provided, comprising protection element 40, having distal open apex 44 fixedly coupled to a distal region of shaft 35. Protection element 40 comprises braid 41, which has fine pores enabling its use as a filter. Actuator 50 is slid over shaft 35 into abutment with proximal open apex 46. The clinician pushes on actuator 50 while pulling on shaft 35 until the normally open configuration of protection element 40 is transformed into a closed configuration with a reduced profile. In this condition, protection apparatus 30 is inserted into the patient's vasculature and advanced there through until protection element 40 is located in an artery immediately downstream of a narrowing to be treated. Actuator 50 is withdrawn over shaft 35, allowing protection element 40 to expand itself into sealing engagement with the artery. A PTCA catheter, with its balloon deflated, is slid over shaft 35 until the balloon is within the targeted narrowing. The PTCA balloon is inflated to dilate the narrowing, and any embolic debris generated thereby is collected by protection element 40. The PTCA balloon is deflated and the catheter is withdrawn. Actuator 50 is re-inserted over shaft 35 to transform protection element 40 from an open configuration to a closed configuration now containing emboli there within. While held in the closed configuration, protection apparatus 30 is withdrawn from the patient.

While the invention has been particularly shown and described with reference to the preferred embodiments thereof, it will be understood by those skilled in the art that various changes in form and detail may be made there in without departing from the spirit and scope of the invention. For example, the invention may be used in any intravascular treatment utilizing a guidewire where the possibility of loosening emboli may occur. Although the description herein illustrates angioplasty and stent placement procedures as significant applications, it should be understood that the present invention is in no way limited to those environments.

We claim:

1. An apparatus for temporary protection adjacent a site of catheter intervention in a body vessel, the apparatus having a flexible, elongate shaft with a distal region, and a protection element mounted about the shaft distal region and being capable of preventing passage of emboli there through, the protection element comprising:
   a self-expanded open configuration having:
      a ring portion capable of sealing engagement with a lumen of the body vessel,
      a generally conical outer body tapering distally from the ring portion to a distal open apex coupled to the shaft, and
      a generally conical inner body extending coaxially within and being shorter than the outer body, the inner body tapering distally from the ring portion to a proximal open apex slidably coupled to the shaft, the inner and outer bodies being connected to each other through the ring portion; and
   a closed configuration wherein the outer body and the ring portion are compacted about the shaft, and the inner body is enveloped within the compacted outer body,
   wherein axial displacement of the proximal open apex towards the distal open apex reversibly transforms the protection element from the open configuration to the closed configuration, and wherein the distal open apex is slidingly coupled to the shaft, which further comprises a stop to prevent distal advancement of the distal open apex there beyond.

2. An apparatus for temporary protection adjacent a site of catheter intervention in a body vessel, the apparatus having a flexible, elongate shaft with a distal region, and a protection element mounted about the shaft distal region and being capable of preventing passage of emboli there through, the protection element comprising:
   a self-expanded open configuration having:
      a ring portion capable of sealing engagement with a lumen of the body vessel,
      a generally conical outer body tapering distally from the ring portion to a distal open apex coupled to the shaft, and
      a generally conical inner body extending coaxially within and being shorter than the outer body, the inner body tapering distally from the ring portion to a proximal open apex slidably coupled to the shaft, the inner and outer bodies being connected to each other through the ring portion; and
   a closed configuration wherein the outer body and the ring portion are compacted about the shaft, and the inner body is enveloped within the compacted outer body,
   wherein axial displacement of the proximal open apex towards the distal open apex reversibly transforms the protection element from the open configuration to the closed configuration;
   the apparatus further comprising an elongate actuator slidably disposed along the shaft and engageable with the proximal open apex to effect movement thereof towards the distal open apex, the actuator having an elongate proximal wire and a short tubular distal section.

3. An apparatus for temporary protection adjacent a site of catheter intervention in a body vessel, the apparatus having a flexible, elongate shaft with a distal region, and a protec tion element mounted about the shaft distal region and being capable of preventing passage of emboli there through, the protection element comprising:

a self-expanded open configuration having:

a ring portion capable of scaling engagement with a lumen of the body vessel, a generally conical outer body tapering distally from the ring portion to a distal open apex coupled to the shaft, and a generally conical inner body extending coaxially within and being shorter than the outer body, the inner body tapering distally from the ring portion to a proximal open apex slidably coupled to the shaft, the inner and outer bodies being connected to each other through the ring portion; and a closed configuration wherein the outer body and the ring portion are compacted about the shaft, and the inner body is enveloped within the compacted outer body, wherein axial displacement of the proximal open apex towards the distal open apex reversibly transforms the protection element from the open configuration to the closed configuration;

the apparatus further comprising an elongate tubular actuator slidably disposed along the shaft and engageable with the proximal open apex to effect movement thereof towards the distal open apex, the actuator having a tubular distal portion being sized to fit within the inner body when the protection element is in the closed configuration, the actuator further comprising a sheath portion surrounding a proximal region of the tubular distal portion to form an annular pocket adapted to enclose at least a proximal portion of the protection element when the protection element is in the closed configuration.

4. The apparatus of claim 3 wherein the sheath portion is flared distally to facilitate engagement with and enclosure of the protection element there within.

\* \* \* \* \*